US012239328B2

(12) United States Patent
Jenkins et al.

(10) Patent No.: US 12,239,328 B2
(45) Date of Patent: Mar. 4, 2025

(54) RIB FRACTURE REPAIR DEVICE

(71) Applicants: The Trustees of Indiana University, Indianapolis, IN (US); Purdue Research Foundation, West Lafayette, IN (US)

(72) Inventors: Peter Clifton Jenkins, Indianapolis, IN (US); Ramses Martinez, West Lafayette, IN (US)

(73) Assignees: The Trustees of Indiana University, Bloomington, IN (US); Purdue Research Foundation, West Lafayette, IN (US)

( * ) Notice: Subject to any disclaimer, the term of this patent is extended or adjusted under 35 U.S.C. 154(b) by 313 days.

(21) Appl. No.: 17/920,089

(22) PCT Filed: Apr. 23, 2021

(86) PCT No.: PCT/US2021/028828
§ 371 (c)(1),
(2) Date: Oct. 20, 2022

(87) PCT Pub. No.: WO2021/216992
PCT Pub. Date: Oct. 28, 2021

(65) Prior Publication Data
US 2023/0248372 A1 Aug. 10, 2023

Related U.S. Application Data

(60) Provisional application No. 63/014,582, filed on Apr. 23, 2020.

(51) Int. Cl.
*A61B 17/16* (2006.01)
*A61B 17/00* (2006.01)
*A61B 90/00* (2016.01)

(52) U.S. Cl.
CPC .............. *A61B 17/1693* (2013.01); *A61B 2017/00238* (2013.01); *A61B 2017/00314* (2013.01);
(Continued)

(58) Field of Classification Search
CPC . A61B 17/16; A61B 17/1633; A61B 17/1693; A61B 17/1631; A61B 17/80; A61B 17/8076
See application file for complete search history.

(56) References Cited

U.S. PATENT DOCUMENTS 6,447,514 B1   9/2002 Stalcup et al.
2011/0295261 A1  12/2011 Germain
(Continued)

FOREIGN PATENT DOCUMENTS

CN   208942242 U   6/2019
WO   2018/160269 A1   9/2018

OTHER PUBLICATIONS

International Search Report and Written Opinion received for PCT Patent Application No. PCT/US21/28828, mailed on Aug. 20, 2021, 7 pages.
(Continued)

*Primary Examiner* — Christopher J Beccia
(74) *Attorney, Agent, or Firm* — Faegre Drinker Biddle & Reath LLP (57) ABSTRACT

The device of the present disclosure is configured for laparoscopic use, particularly to insert a fastener into a plate at an angle of up to 180° from the plane of insertion. The device is further configured to carry a plurality of fasteners, a tightening tool, a cutting device, and tweezers simultaneously to facilitate a rapid procedure while lessening the chance of infection by limiting the amount of times the device must be removed and re-inserted.

20 Claims, 7 Drawing Sheets

(52) U.S. Cl.
CPC .............. *A61B 2017/00336* (2013.01); *A61B 2017/00353* (2013.01); *A61B 2017/00893* (2013.01); *A61B 2090/064* (2016.02); *A61B 2090/067* (2016.02)

(56) References Cited

U.S. PATENT DOCUMENTS

| | | |
|---|---|---|
| 2012/0029420 A1 | 2/2012 | Rittman, III et al. |
| 2012/0232552 A1 | 9/2012 | Morgenstern Lopez et al. |
| 2014/0257296 A1 | 9/2014 | Morgenstern Lopez |
| 2014/0288561 A1 | 9/2014 | Tallarida et al. |
| 2014/0336653 A1 | 11/2014 | Bromer |
| 2019/0069908 A1 | 3/2019 | Zilberman et al. |
| 2020/0078096 A1 | 3/2020 | Barbagli et al. |

OTHER PUBLICATIONS

Supplementary European Search Report and Search Opinion Received for EP Application No. 21792700.3, mailed on Mar. 27, 2024, 7 pages.

RIB FRACTURE REPAIR DEVICE

RELATED APPLICATIONS

The present application is a 371 U.S. National Phase of International PCT Application No. PCT/US2021/028828, filed Apr. 23, 2021, which claims the benefit of U.S. Provisional Application No. 63/014,582, filed Apr. 23, 2020, the entire disclosures of which isare hereby expressly incorporated herein by reference in their entirety.

FIELD OF THE DISCLOSURE

The present disclosure relates generally to medical devices, and, more particularly, to medical devices for use in thoracoscopic procedures for repairing bone fractures, and specifically for repairing rib fractures.

BACKGROUND OF THE DISCLOSURE

Rib fractures are the most common type of traumatic injury associated with morbidity and mortality, and repair of rib fractures is typically involved and difficult. Currently, a highly invasive surgical procedure, open reduction and internal fixation ("ORIF"), serves as the leading method for repair complex or multiple rib fractures with improved outcomes. However, ORIF requires large incisions and chest wall dissection that is associated with extensive pain, denervation of the chest wall, shoulder dysfunction, and infection. During the ORIF procedure, fractured ribs are aligned and metal plates are then screwed into place on the outside of the chest over the ribs to support the broken bones during healing.

Minimally invasive techniques to repair broken ribs and replace the ORIF procedure for many rib fracture repairs are desired. One technique may include attaching metal plates on the inside of the chest wall rather than the outside of the chest wall to avoid damage to nerves, muscles, and other body structures found on the outer surface of the chest wall. The use of absorbable polymer plates to repair ribs instead of permanent metallic plates has also been explored. However, these methods are generally beyond the capability of modern equipment. For example, current intrathoracic drills are limited to a 60° range of motion.

SUMMARY OF THE DISCLOSURE

The device of the present disclosure is configured for laparoscopic use, particularly to insert a fastener into a plate at an angle of up to 180° from the plane of insertion. The device is further configured to carry a plurality of fasteners, a tightening tool, a cutting device, and tweezers simultaneously to facilitate a rapid procedure while lessening the chance of infection by limiting the amount of times the device must be removed and re-inserted.

In an exemplary embodiment of the present disclosure, a device for performing a plurality of remote operations is disclosed. The device comprises a handle, a loading tool extending from the handle, and a spine coupled to the loading tool. The spine is comprised of a plurality of chain segments, wherein each chain segment is removably coupled to an adjacent chain segment and the chain segments collectively define a series of operational openings. A flexible shaft is disposed through the operational openings of the chain segments and is configured to be removed form the spine without movement of the spine. A drill is disposed on a distal end of the flexible shaft and is configured to couple to a plurality of tools. An outer sheath is positioned around the spine.

The outer sheath may include a plurality of grooves, and the plurality of grooves may contain a therapeutic agent. The drill may be configured to couple to a plurality of tools at one time. The plurality of tools may include at least one of a tweezer tool, a scissor tool, and a screw drill assembly. The flexible shaft may be configured to rotate within the spine without corresponding movement of the spine. The spine may be configured to bend at an angle up to 180° relative to a tip of the loading tool. The device may further comprise a strain sensor coupled to the outer sheath, the strain sensor configured to indicate a bending angle of the outer sheath.

Additional features and advantages of the present disclosure will become apparent to those skilled in the art upon consideration of the following detailed description of the illustrative embodiments exemplifying the disclosure as presently perceived.

BRIEF DESCRIPTION OF THE DRAWINGS

The detailed description of the drawings particularly refers to the accompanying figures in which:

FIG. 6B illustrates a method of utilizing the screw drill assembly of FIG. 6A to affix a screw to a plate;

Corresponding reference characters indicate corresponding parts throughout the several views. Although the drawings represent embodiments of various features and components according to the present disclosure, the drawings are not necessarily to scale and certain features may be exaggerated in order to better illustrate and explain the present disclosure. The exemplification set out herein illustrates an embodiment of the invention, and such an exemplification is not to be construed as limiting the scope of the invention in any manner.

DETAILED DESCRIPTION

The embodiments of the disclosure described herein are not intended to be exhaustive or to limit the disclosure to the precise forms disclosed. Rather, the embodiments described herein enable one skilled in the art to practice the disclosure.

Figure 1:
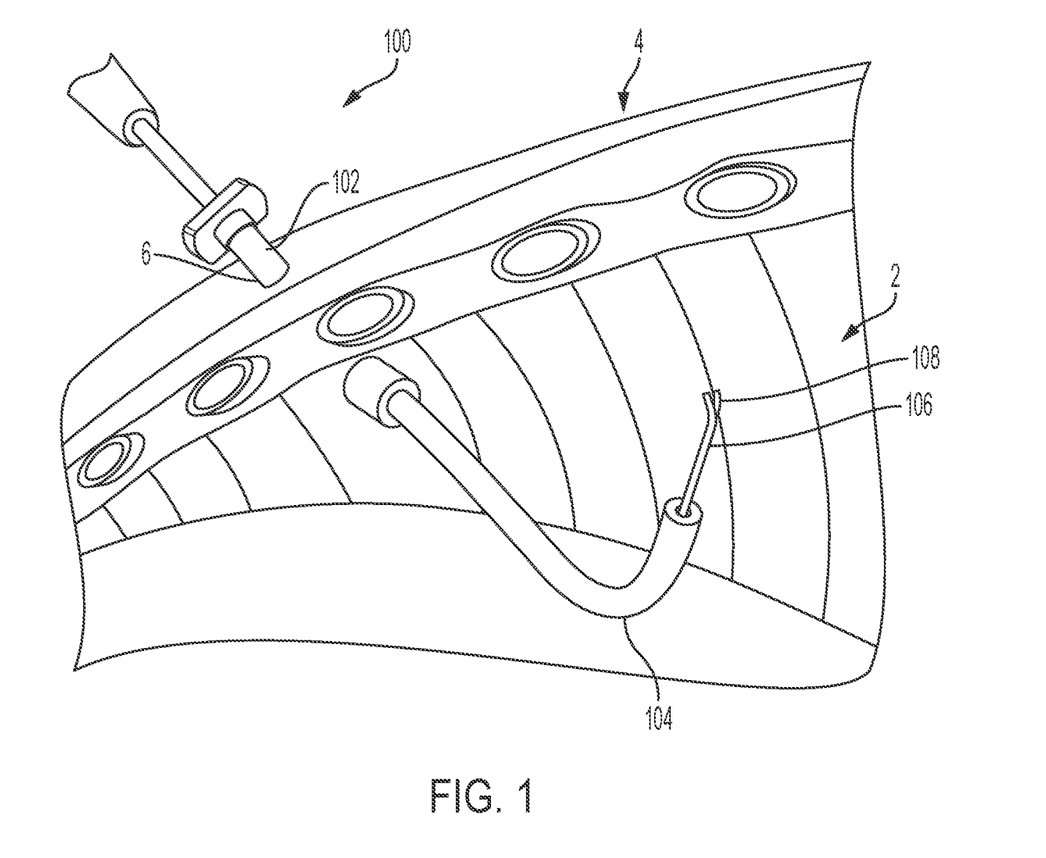
FIG. 1 illustrates a device of the present disclosure utilized within a chest cavity of a patient, the device including a flexible shaft positioned within the interior of the chest cavity and a drill disposed on a distal end of the flexible shaft for use within the chest cavity of the patient.

FIG. 1 illustrates a device 100 of the present disclosure being used laparoscopically within a chest cavity 2 of a patient 4 for a laparoscopic procedure. The device 100 includes an outer sheath 102 laterally surrounding a flexible shaft 104. The flexible shaft 104 includes a drill 106 configured to carry at least one tool 108. As discussed further herein, the at least one tool 108 may include a fastener such as a screw, a nut, a clip, a bolt, an anchor, a pin, or another type of mechanical fastener; a tightening tool such as a screwdriver, a wrench, an Allen wrench, a pair of pliers, or another tool used for tightening; a cutting device such as a pair of scissors, a knife, a blade, or another tool used for cutting; tweezers, or another tool 108. The drill 106 may also be configured to carry multiple tools 108.

In use, the device 100 is inserted through a laparoscopic incision 6 to enter the patient 4 so that the outer sheath 102 is disposed through the laparoscopic incision 6 throughout the laparoscopic procedure. As discussed further herein, the flexible shaft 104 may be controlled by the device 100 to complete the laparoscopic procedure without removing and replacing the device through the incision 6. The flexible shaft 104 is configured to be retracted from the chest cavity 2 through the outer sheath 102 so that the tool 108 may be replaced without withdrawing the outer sheath 102 through the laparoscopic incision 6. The flexible shaft 104 may then be returned to the chest cavity 2 to continue the laparoscopic procedure.

Figure 2A:
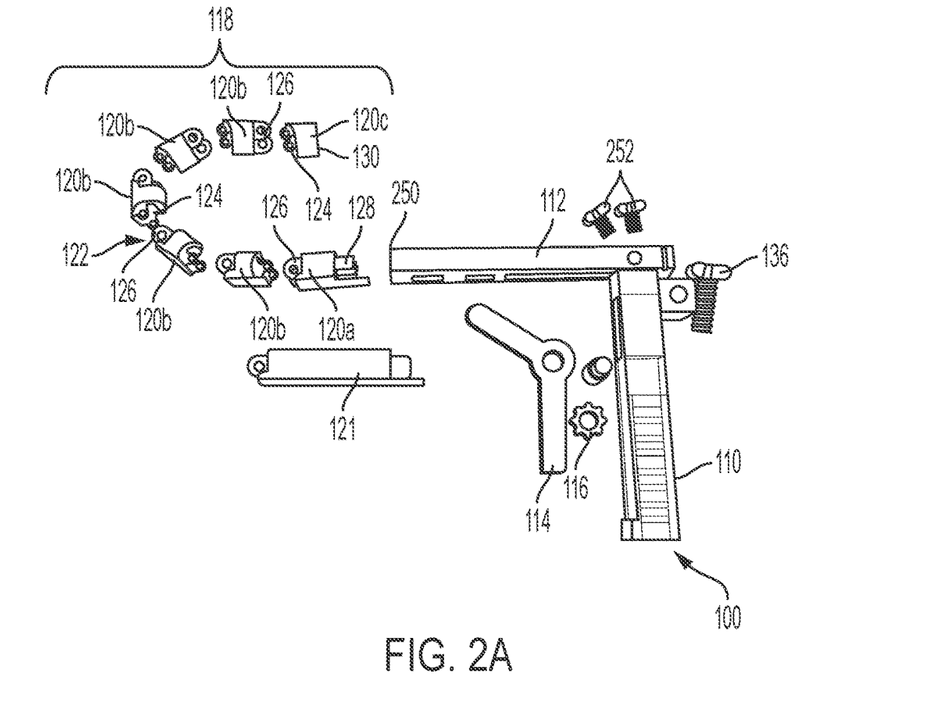
FIG. 2A illustrates an exploded view of the device of FIG. 1, the device including a spine comprised of a plurality of chain segments.

Now referring to FIG. 2A, an exploded view of the device 100 is illustrated. The device 100 is comprised of a handle 110 and a loading tool 112 extending from the handle 110 at a substantially perpendicular angle from the handle 110. In other embodiments, the loading tool 112 extends from the handle 110 at any workable angle. A trigger 114 is coupled to the handle 110 using a fastener, such as nut 116. In other embodiments, the trigger 114 may be coupled to the handle 110 using other methods, including another mechanical fastener such as a screw, a nut, a clip, a bolt, an anchor, a pin, a latch, or another type of mechanical fastener; adhesive; single-piece manufacturing; or other coupling methods known in the art.

Figure 2B:
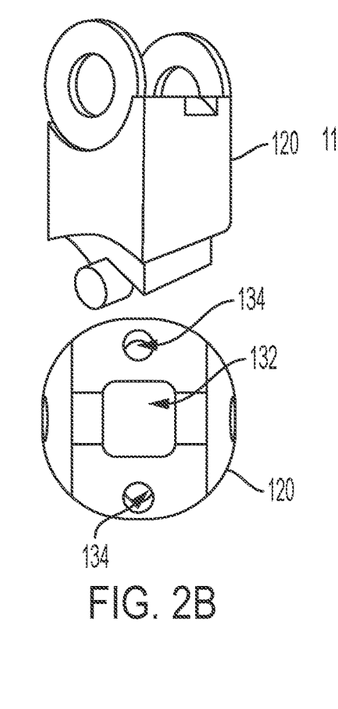
FIG. 2B illustrates a perspective view and a top view of one of the plurality of chain segments of FIG. 2A.

Referring to FIGS. 2A and 2B, the loading tool 112 is coupled to a spine 118 of the outer sheath 102 (FIG. 1). The spine 118 comprises a plurality of chain segments 120, each chain segment 120 defining an operational opening 132 so that when the chain segments 120 are coupled, an operational pathway is formed through the spine 118. Each chain segment 120 further defines at least one driving aperture 134 so that a driving pathway is formed through the spine 118 when the chain segments 120 are coupled. Illustratively, each chain segment 120 defines two driving apertures 134.

Now referring again to FIG. 2A, the first chain segment 120 depending from the loading tool 112, i.e. primary chain segment 120a, is removably coupled to the loading tool 112 via an extension 128 of the primary chain segment 120a to be received within the loading tool 112. The primary chain segment 120a may be coupled to the loading tool 112 using other coupling methods, i.e. mechanical fasteners as mentioned above, a hinge, adhesive, or other coupling methods known in the art. In yet other embodiments, the primary chain segment 120a may be fixedly coupled to the loading tool 112 via an adhesive, single-piece manufacturing, or other coupling methods known in the art.

The chain segment 120 most distal from the loading tool 112, i.e. end chain segment 120c, has a soft, blunt distal end 130 for insertion through the laparoscopic incision 6 (FIG. 1). The chain segments 120 between the primary chain segment 120a and the end chain segment 120c, i.e. mid-chain segments 120b, are removably, rotatably coupled together via hinges 122, wherein a knuckle portion 124 of the hinge 122 is located on one chain segment 120, and the pin portion 126 of the hinge 122 is located on an adjacent chain segment 120, wherein the pin portion 126 serves as an axis of rotation between the adjacent chain segments 120. The end chain segment 120c is likewise coupled to an adjacent chain segment 120 via a hinge 122. Illustratively, the end chain segment 120c includes a knuckle portion 124, but the end chain segment 120c may be modified to instead include a pin portion 126. The primary chain segment 120a is also coupled to an adjacent chain segment 120 via a hinge 122. Illustratively, the primary chain segment 120a includes a pin portion 126, but the primary chain segment 120a may be modified to include a knuckle portion 124.

The number of chain segments 120 used to make up the spine 118 may vary depending on the desired length of the outer sheath 102. For example, in some embodiments, the spine 118 may include a plurality of mid-chain segments 120b. In other embodiments, the spine 118 may include a single mid-chain segment 120b. In yet other embodiments, the spine 118 may omit mid-chain segments 120b and include only the primary chain segment 120a and the end chain segment 120c. In further embodiments, the primary chain segment 120a may serve as both the primary chain segment 120a and the end chain segment 120c and be modified as such, i.e. including both an extension 128 and a blunt distal end 130. The chain segments 120 are removably coupled to each other so that chain segments 120 may be added and removed as desired. Furthermore, long chain segments 121 may replace illustrated chain segments 120 in the event further distance between hinges 122 is desired. Ideally, the chain segments 120 are coupled in a manner that allows the spine to be manipulated at an angle of up to and including 180° from the plane of insertion, or a tip 250 of the loading tool 112.

Figure 2C:
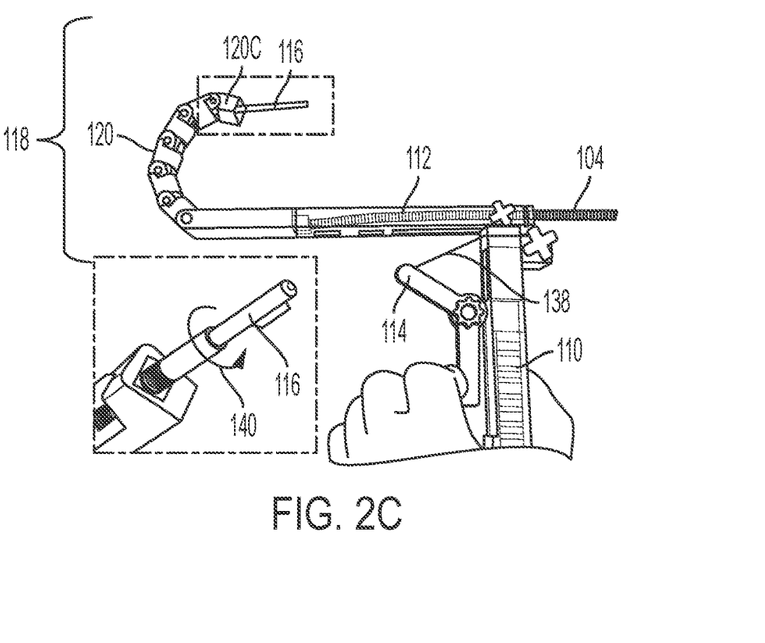
FIG. 2C illustrates an assembled plan view of the device of FIG. 2A, further illustrating the rotational capability of the flexible shaft and the drill.

Referring to FIGS. 2A-2C, a driving thread 138 is disposed through the driving pathway defined by the driving openings 134 of the chain segments 120 and is further disposed through the handle 110 to couple to the trigger 114 so that manipulation of the trigger 114 may manipulate the spine 118. The flexible shaft 104 is disposed through the operational pathway defined by the operational openings 132 of the chain segments 120 so that the flexible shaft 104 is extendible beyond the end chain segment 120c for manipulation during the laparoscopic procedure. The flexible shaft 104 is disposed through the spine 118 in a manner that allows the flexible shaft 104 to move within the spine 118. For example, the flexible shaft 104 is retractable, insertable, and rotatable, as shown by arrow 140, within the spine 118 for use during the laparoscopic procedure. A driving screw 136 drives an operational thread 194 (FIGS. 4A-6D) to control the tool 108 coupled to the drill 106 disposed at a distal end of the flexible shaft 104. The flexible shaft extends beyond the proximal end 142 of the loading tool 112 of the device 100 for manipulation by a user during the procedure. Lock screws 252 may facilitate assembly of the device 100 by holding the outer sheath 102 (FIGS. 3A-3B) in place over the loading tool 112 if desired.

Figure 3A:
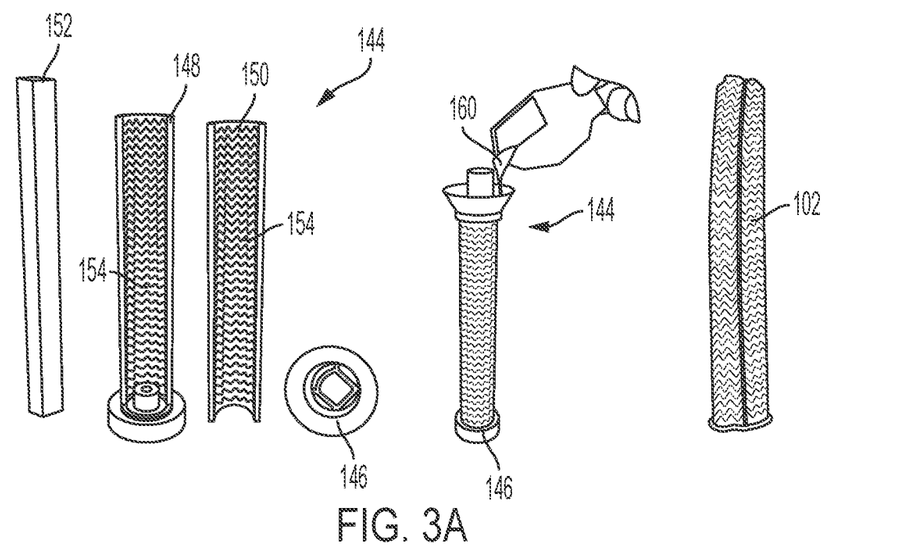
FIG. 3A illustrates a method of manufacturing an outer sheath, wherein the outer sheath is configured to be positioned around the spine of the device of FIG. 2A.
Figure 3B:
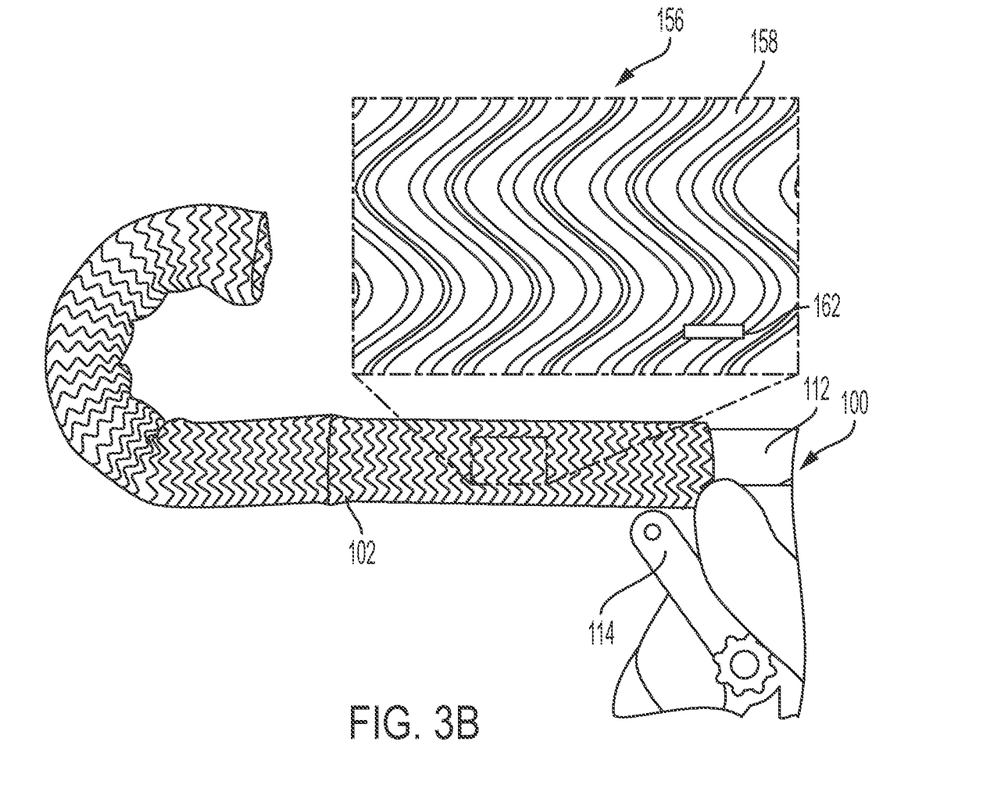
FIG. 3B illustrates the outer sheath positioned around the spine of the device, further illustrating a plurality of grooves on an outer surface of the outer sheath and a strain sensor coupled to the outer sheath.

Now referring to FIGS. 3A-3B, a method for manufacturing the outer sheath 102 is shown. A mold 144 for the outer sheath 102 is formed from four separate parts, including a base mold 146, a first longitudinal mold 148, a second longitudinal mold 150, and a central template 152. The central template 152 is sized and shaped to ensure the resulting outer sheath 102 is configured to receive the spine 118 (FIG. 2A) of the device 100. The first longitudinal mold 148 and the second longitudinal mold 150 include groove projections 154 which result in grooves 156 on the outer surface 158 of the outer sheath 102 as described further herein.

The corresponding parts of the mold 144 may be manufactured via additive printing, such as three-dimensional (3D) printing. The corresponding parts of the mold 144 may otherwise be fabricated via known manufacturing processes. Three-dimensional printing illustratively uses digital three-dimensional models (such as those created from scans or computer-assisted design software) to produce a three-dimensional object through the creation of layers by a three dimensional printer. Several different three-dimensional printing technologies are known, including selective laser sintering, fused deposition modeling, direct metal laser sintering, electron beam additive manufacturing technology, and stereolithography.

Many different materials can be used, individually or mixed, to create three dimensionally printed objects, including acrylonitrile butadiene styrene plastic, polylactic acid, polycaprolactone, polyamide, glass filled polyamide, epoxy resins, silver, titanium, steel, wax, photopolymers, polycarbonate, stainless steels, INCONEL, brass, bronze, and other materials that may be powder based. Where direct metal laser sintering is used with application-suitable corrosion resistant materials, non-sintered metallic powder can be removed with a stream of pressurized fluid, and internal channels treated with acid etching or abrasive slurries. Multimedia three-dimensional printing is also known, so that in some embodiments, mixed metallic-plastic items may be fabricated. The material may be biocompatible to facilitate use within the body of a patient.

Referring to FIG. 3A, once assembled, the mold 144 is configured to receive a liquid configuration of outer sheath material 160. In the illustrated embodiment, the outer sheath material 160 comprises a polymer, such as an elastomer, and preferably has a hardness below the Shore A scale once cured. In other words, the outer sheath material 160 only fractures above a maximum strain of at least 900% once cured. More specifically, the outer sheath material 160 may comprise Ecoflex 00-30. Once the mold 144 contains an appropriate amount of the liquid configuration of outer sheath material 160, the outer sheath material 160 contained within the mold 144 is cured to create the solid outer sheath 102. For example, the outer sheath material 160 is cured at about 60° C. for about 15 minutes and then cooled to room temperature. The outer sheath material 160 may be cured at another appropriate temperature or for another appropriate amount of time depending on the type of material used. Once cooled, the base mold 146, the first longitudinal mold 148, the second longitudinal mold 150, and the central template 152 is removed from the outer sheath 102. Now referring to FIG. 3B, as discussed above, the outer surface 158 of the outer sheath 102 includes a plurality of grooves 156. The grooves 156 may hold a therapeutic agent composition to assist with infection prevention of the laparoscopic incision 6 (FIG. 1). The grooves 156 may further operate to collect and remove bone dust from the chest cavity 2 (FIG. 1) or other body cavity of the patient.

Figure 3C:
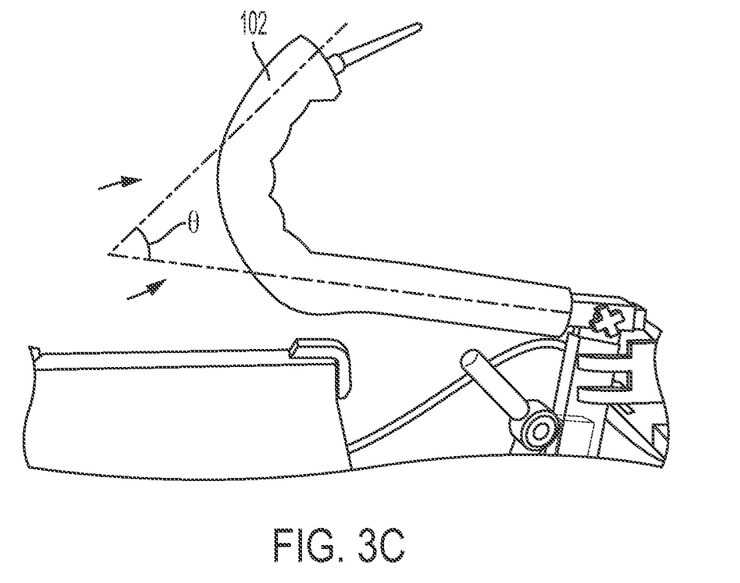
FIG. 3C illustrates an angle measurement of the spine of the device, wherein the angle measurement of the spine may vary.

During the manufacturing process of the outer sheath 102, the outer sheath material 160 preferably forms microchannels within the material throughout the outer sheath 102. The microchannels are configured to deform, flex, stretch, and compress as the outer sheath 102 is manipulated. A strain sensor 162, such as a Eutectic Gallium-Indium ("EGaIn") sensor, is attached to the outer sheath 102. EGaIn is injected into the microchannels formed by the outer sheath material 160 so that when the outer sheath 102 is manipulated, the outer sheath material 160 stretches to deform and squeeze the EGaIn within the microchannels. Specifically, EGaIn is injected into the microchannels and entrapped air is evacuated from the microchannels. Wires are then inserted into ports of the microchannels and the interface between the microchannels and the wires are sealed. As the geometry of the microchannels changes, EGaIn resistance changes. The strain sensor 162 is attached to the inside of the outer sheath 102 in a manner that allows the outer sheath 102 to receive the spine 118. The strain sensor 162 measures the change in EGaIn resistance within the microchannels, allowing the user to calculate the bending angle of the outer sheath 102 as illustrated in FIG. 3C. For example, when the outer sheath 102 is disposed on the spine 118 (FIG. 2A) of the device 100, as the spine 118 (FIG. 2A) is manipulated within the patient 4 (FIG. 1), the outer sheath 102 is resultingly actuated, and the strain sensor 162 measures the change in EGaIn resistance, communicating the degree of the bending angle of the spine 118 and the outer sheath 102 to the user.

Figure 3D:
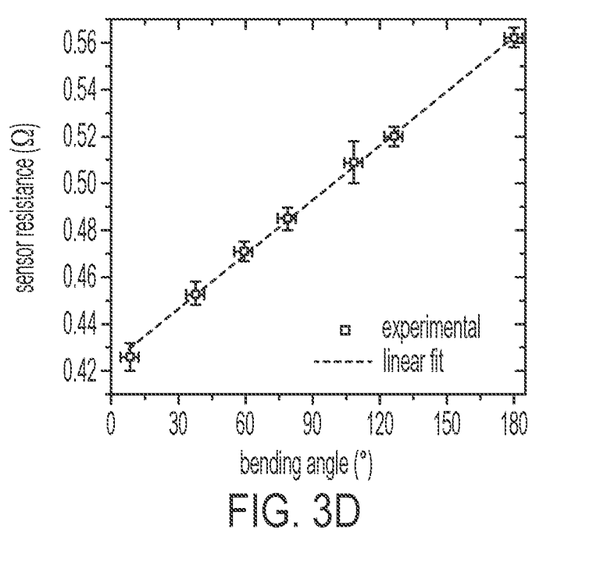
FIG. 3D is a graph illustrating the relationship between a measured sensor resistance of the outer sheath and a bending angle of the spine.

FIG. 3D shows the linear relationship between the measured sensor resistance and the bending angle of the spine 118. For example, when the sensor resistance is measured between 0.44Ω and 0.46Ω, the bending angle of the spine 118 may be between 30° and 45° and may be about 38°. When the sensor resistance is measured between 0.46Ω and 0.48Ω, the bending angle of the spine 118 may be between 45° and 75° and may be about 60°. When the sensor resistance is measured between 0.48Ω and 0.50Ω, the bending angle of the spine 118 may be between 60° and 90° and may be about 75°. When the sensor resistance is measured between 0.50Ω and 0.52Ω, the bending angle of the spine 118 may be between 90° and 120° and may be about 95°. When the sensor resistance is measured between 0.51Ω and 0.53Ω, the bending angle of the spine 118 may be between 105° and 135° and may be about 128°. When the sensor resistance is measured between 0.55Ω and 0.57Ω, the bending angle of the spine 118 may be between 165° and 195° and may be about 178°.

Figure 4A:
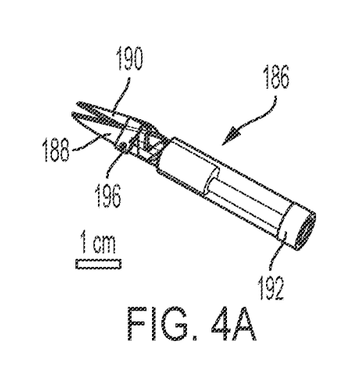
FIG. 4A illustrates a scissor tool configured to couple to the drill of the device of FIG. 1.
Figure 4B:
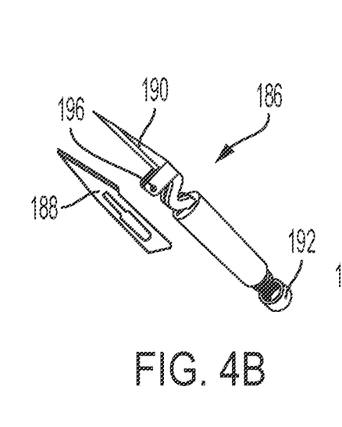
FIG. 4B illustrates an exploded view of the scissor tool of FIG. 4A.
Figure 4C:
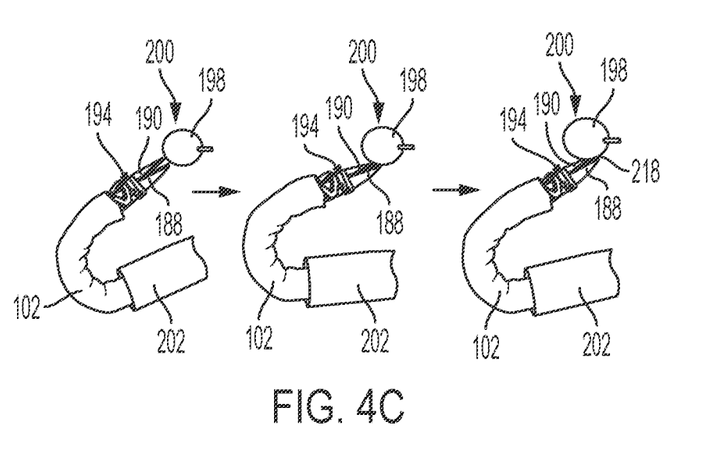
FIG. 4C illustrates a method of utilizing the scissor tool of FIG. 4A.

Now referring to FIGS. 4A-4C, a scissor tool 186 is shown. The scissor tool 186 comprises a blade 188, a compliant element 190 controllable via an operational thread 194 (FIG. 4C), and a locking nut 192 for coupling the scissor tool 186 to the drill 106 (FIG. 2C). The components of the scissor tool 186, i.e. the blade 188, the compliant element 190, and the locking nut 192, are further illustrated in the exploded view of the scissor tool 186 in FIG. 4B.

FIG. 4C illustrates a method of utilizing the scissor tool 186. As shown, the operational thread 194 is coupled to the compliant element 190. The operational thread 194 may be tied to the compliant element 190 by disposing the operational thread 194 through an eye 196 (FIGS. 4A, 4B) of the compliant element 190 and tying the operational thread 194 for security. In other embodiments, the operational thread 194 may be coupled to the compliant element 190 via other methods known in the art, such as, for example, adhesive or a mechanical fastener. In yet other embodiments, the operational thread 194 may be tied to the compliant element 190 without the use of an eye 196. As discussed above, the operational thread 194 is then disposed through the spine 118 (FIG. 2A) and the loading tool 112 (FIG. 2A) of the device 100 (FIG. 2A) for manipulation by a user.

To illustrate the method of utilizing the scissor tool 186, skin 198 of a grape 200 is cut as shown in FIG. 4C. For example, the blade 188 and the compliant element 190 is placed on the skin 198 of the grape 200. As the user actuates the operational thread 194, the compliant element 190 moves relative to the blade 188 so that the scissor tool 186 operates similarly to a pair of conventional scissors, forming a cut portion 218 of the skin 198. In other embodiments, the operational thread 194 may be coupled to a trigger, such as the trigger 114 (FIG. 2A) or another trigger, to operate the scissor tool 186. In yet other embodiments, the operational thread 194 is coupled to the driving screw 136 (FIG. 2A) so that rotation of the driving screw 136 (FIG. 2A) operates the scissor tool 186. Additionally, the device 100 may be utilized in cooperation with a trocar 202 as illustrated in FIG. 4C, FIG. 5C, and FIG. 6C discussed further herein.

Figure 5A:
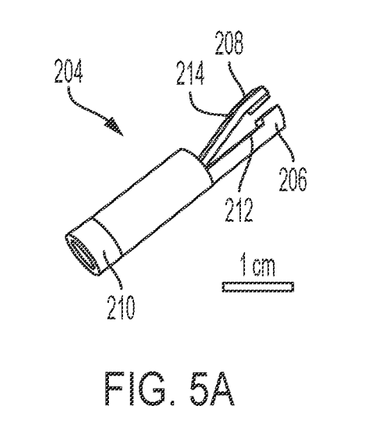
FIG. 5A illustrates a tweezer tool configured to couple to the drill of the device of FIG. 1.
Figure 5B:
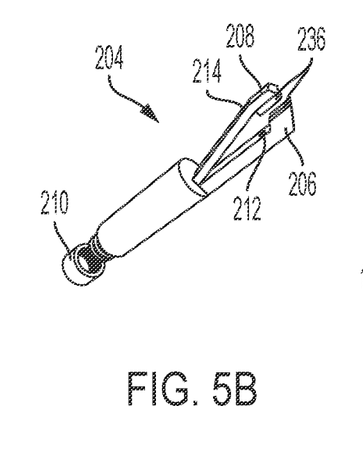
FIG. 5B illustrates an exploded view of the tweezer tool of FIG. 5A.
Figure 5C:
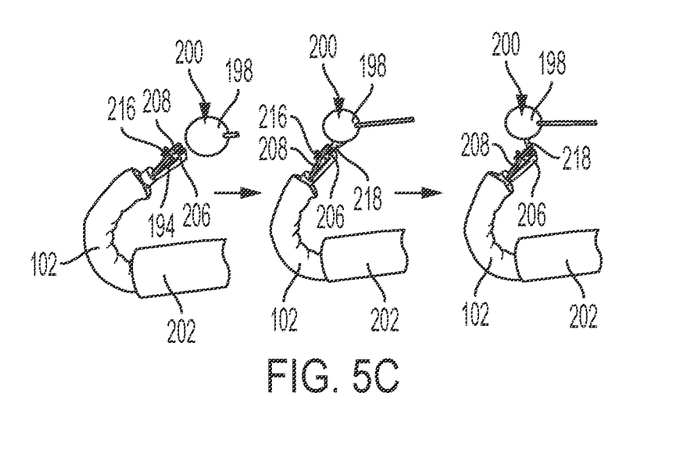
FIG. 5C illustrates a method of utilizing the tweezer tool of FIG. 5A.
Figures 6A, 6C:
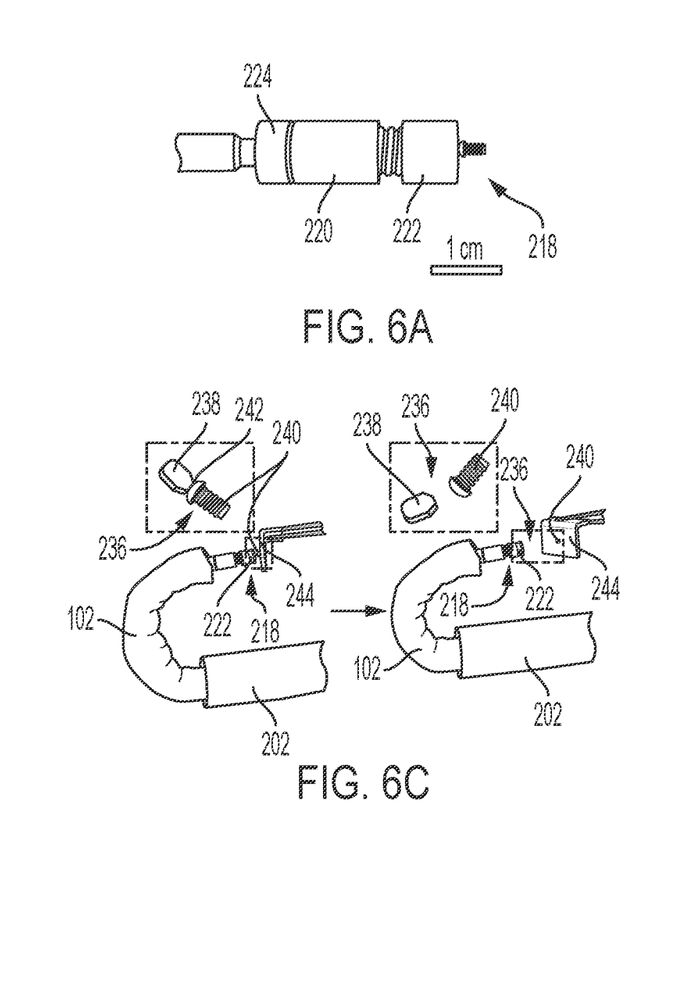
FIG. 6A illustrates a screw drill assembly configured to couple to the drill of the device of FIG. 1.
FIG. 6C illustrates the screw of FIG. 6B affixed to the plate.

Now referring to FIGS. 5A-5C, a tweezer tool 204 is shown. The tweezer tool 204 comprises a fixed arm 206, a compliant arm 208 controllable via an operational thread 194 (FIG. 5C), and a locking nut 210 for coupling the tweezer tool 204 to the drill 106 (FIG. 2C). The components of the tweezer tool 204, i.e. the fixed arm 206, the compliant arm 208, and the locking nut 210, are further illustrated in the exploded view of the tweezer tool 204 in FIG. 5B. In the illustrative embodiment, the tips 236 of the fixed arm 206 and the compliant arm 208 are zig-zag in shape to facilitate the grasping of an object. In other embodiments, the tips 236 of the fixed arm 206 and the compliant arm 208 may be smooth or form another shape.

FIG. 5C illustrates a method of utilizing the tweezer tool 204. As shown, the operational thread 194 may be tied to the compliant arm 208 and the fixed arm 206 by disposing the operational thread 194 through an eye 212 of the fixed arm 206 (FIGS. 5A, 5B) and an eye 214 of the compliant arm 208 (FIGS. 5A, 5B) and tying a knot 216 on the operational thread 194 for security. When the operational thread 194 is actuated, the knot 216 transfers pressure onto the compliant arm 208 and moves the compliant arm 208 relative to the fixed arm 206. In other embodiments, the operational thread 194 may be coupled to the compliant arm 208 via other methods known in the art, such as, for example, adhesive or a mechanical fastener. In yet other embodiments, the operational thread 194 may be tied to the compliant arm 208 without the use of the eye 214, the use of the eye 212, and/or the use of the fixed arm 206. As discussed above, the operational thread 194 is then disposed through the spine 118 (FIG. 2A) and the loading tool 112 (FIG. 2A) of the device 100 (FIG. 2A) for manipulation by a user. In other embodiments, the operational thread 194 may be coupled to a trigger, such as the trigger 114 or another trigger, to operate the tweezer tool 204. In yet other embodiments, the operational thread 194 is coupled to the driving screw 136 (FIG. 2A) so that rotation of the driving screw 136 (FIG. 2A) operates the tweezer tool 204.

To illustrate the method of utilizing the tweezer tool 204, the cut portion 218 of the skin 198 of the grape 200 is peeled away as shown in FIG. 5C. For example, the cut portion 218 of the skin 198 of the grape 200 is positioned between the fixed arm 206 and the compliant arm 208. The operational thread 194 is actuated so that the compliant arm 208 moves relative to the fixed arm 206, pinching the cut portion 218 between the compliant arm 208 and the fixed arm 206. The tweezer tool 204 can then be further actuated via the spine 118 (FIG. 2A) to peel the skin 198 of the grape 200.

Figure 6B:
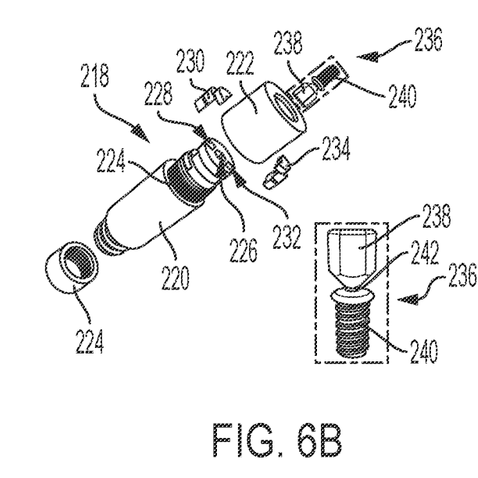
FIG. 6B illustrates an exploded view of the screw drill assembly of FIG. 6A.
Figure 6D:
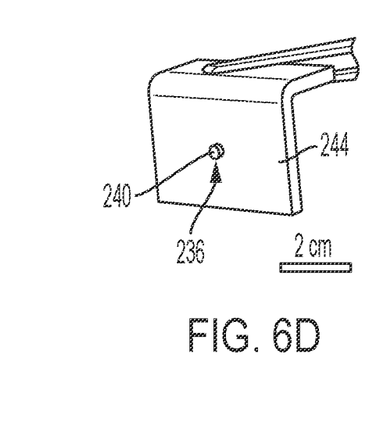

Referring now to FIGS. 6A-6D, a resorbable screw drill assembly 218 is illustrated. The screw drill assembly 218 includes a screwdriver 220, a cap 222, and a locking nut 224 for coupling the screw drill assembly 218 to the drill 106 (FIG. 2C). As shown in FIG. 6B, the screwdriver 220 defines threading 224 to facilitate the coupling of the cap 222 with the screwdriver 220. The cap 222 and the screwdriver 220 may be removably coupled in other ways as known to one skilled in the art. For example, the cap 222 and the screwdriver 220 may be coupled using any of a variety of mechanical fasteners or via interference fit. The screwdriver 220 further defines a screw aperture 226, a first clamp mount 228 configured to receive a first clamp 230, and a second clamp mount 232 configured to receive a second clamp 234.

A screw 236 for use with the screw drill assembly 218 is further illustrated. The screw 236 may be comprised of any of the materials described above, including bioresorbable material, and includes a head portion 238 and an operable portion 240, wherein the head portion 238 and the operable portion 240 meet at a breaking point 242. During assembly, the head portion 238 of the screw 236 is inserted into the screw aperture 226 of the screwdriver 220 so that the operable portion 240 of the screw 236 extends from the screwdriver 220. The first clamp 230 and the second clamp 234 are mounted within the first clamp mount 228 and the second clamp mount 232 respectively, the first clamp 230 and the second clamp 234 cooperating to hold the screw 236 in place within the screw aperture 226 via the head portion 238 of the screw 236. The cap 222 is mounted on the screwdriver 220 via the threading 224 to fix the clamps 230, 234 in place. As shown in FIG. 6A, the operable portion 240 of the screw 236 extends beyond the cap 222 to engage with a plate 244 (FIGS. 6C, 6D) as further described herein.

FIG. 6C illustrates the method of utilizing the screw drill assembly 218. The mounted screw 236 is positioned in place adjacent the plate 244. Rotation of the flexible shaft 104 (FIG. 1) rotates the drill 106 (FIG. 2C), which rotates the screwdriver 220, thereby rotating the screw 236. When the screw 236 has been rotated so that the operable portion 240 of the screw 236 is fully affixed to the plate 244, further rotation of the flexible shaft 104 will cause the operable portion 240 and the head portion 238 of the screw 236 to break at the breaking point 242 via torque-controlled release, allowing the user to extricate the head portion 238 from the patient while leaving the operable portion 240 in position within the plate 244. In the illustrated embodiment, the screw 236 can withstand a torque limit of less than 15.8 before the breaking point 242 of the screw 236 gives way to separate the operable portion 240 and the head portion 238 of the screw.

The properties of the tools discussed herein can be changed by changing the concentration of the bioresorbable polymers used, as discussed further herein. Specifically, the concentration of the bioresorbable polymers used to manufacture the screw 236 may be changed while also introducing bubbles into the material mixture to facilitate a "clean break" at the breaking point 242 of the screw 236. This allows the screw 236 to break at the breaking point 242 without creating ductile artifacts, allowing the break to occur without additional application of heat to melt any peaks remaining on the operable portion 230 of the screw after the break occurs.

Figure 7A:
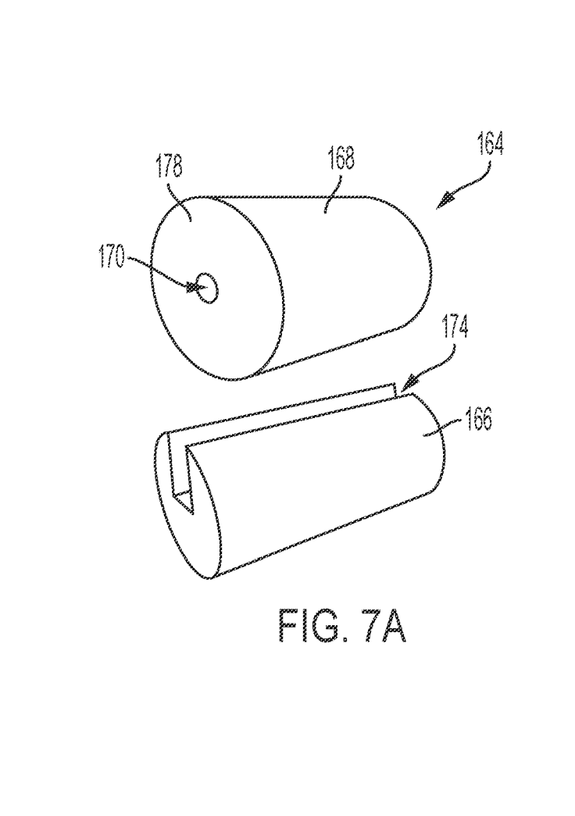
FIG. 7A illustrates a partially exploded view alternate embodiment of a drill of the device of FIG. 1, the drill including a case and a tool driver.
Figure 7B:
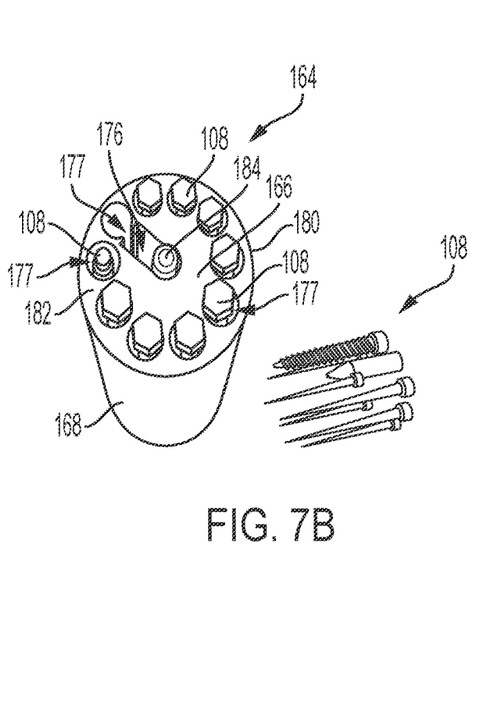
FIG. 7B illustrates the tool driver of FIG. 7A disposed within the case of FIG. 7A for use, the case including a plurality of storage apertures to receive a plurality of tools.
Figure 7C:
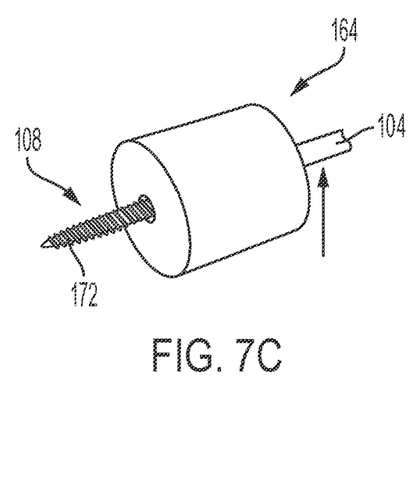
FIG. 7C illustrates the drill of FIG. 7A coupled to the flexible shaft, the drill including a screw disposed within the tool driver and the case.

Now referring to FIGS. 7A-7C, another drill embodiment 164 is shown. As shown in FIG. 7A, the drill 164 is comprised of a tool driver 166 and a case 168 defining a cavity 176 (FIG. 7B) configured to receive the tool driver 166 as illustrated further in FIG. 7B. The case 168 defines an aperture 170 on a first end 178 of the case 168, the aperture 170 configured to expose a working portion 172 (FIG. 7C) of the tool 108 (FIG. 7C) being utilized. The tool driver 166 defines a trough 174 at least partially aligned with the aperture 170 of the case 168. The trough 174 is configured to receive at least a portion of the tool 108 (FIG. 7C) and may be further configured to receive a portion of the flexible shaft 104 (FIG. 7C).

FIG. 7B illustrates the tool driver 166 positioned within the case 168. As shown, the case 168 includes a plurality of storage apertures 177 positioned around a perimeter 180 of a second end 182 of the case 168, each storage aperture 177 configured to receive a tool 108 when the respective tool 108 is not in use. An exemplary illustration of a plurality of tools 108 that may be stored within the storage apertures 177 of the case 168 is provided. The tool driver 166 may include a spring-loaded mechanism 184 positioned within the trough 174 of the tool driver 166 to facilitate the replacement of one tool 108 with another tool 108. The spring-loaded mechanism 184 may further facilitate the coupling of the tool 108 with the flexible shaft 104 (FIG. 7C) to allow control of the tool 108 using the flexible shaft 104 (FIG. 7C). The tool driver 166 is configured to rotate within the case 168 if desired for operation of the tool 108.

FIG. 7C illustrates the drill embodiment 164 assembled with the flexible shaft 104. As shown, a tool 108 is positioned within the trough 174 of the tool driver 166 (FIG. 7A) so that the working portion 172 of the tool 108 is disposed through the aperture 170 of the case 168 for utilization. The flexible shaft 104 is coupled to the tool 108 via the trough 174 of the tool driver 166 (FIG. 7A) for operation.

The corresponding parts of any of the tools described herein may be manufactured via additive printing, such as three-dimensional (3D) printing. The corresponding parts of the tools described herein may otherwise be fabricated via known manufacturing processes. As discussed above in relation to the mold 144 (FIGS. 3A-3B), three-dimensional printing illustratively uses digital three-dimensional models (such as those created from scans or computer-assisted design software) to produce a three-dimensional object through the creation of layers by a three-dimensional printer. Several different three-dimensional printing technologies are known, including selective laser sintering, fused deposition modeling, direct metal laser sintering, electron beam additive manufacturing technology, and stereolithography.

Many different materials can be used to create three dimensionally printed objects, including acrylonitrile butadiene styrene plastic, polylactic acid, polyamide, glass filled polyamide, epoxy resins, silver, titanium, steel, wax, photopolymers, polycarbonate, stainless steels, INCONEL, brass, bronze, and other materials that may be powder based. Where direct metal laser sintering is used with application-suitable corrosion resistant materials, non-sintered metallic powder can be removed with a stream of pressurized fluid, and internal channels treated with acid etching or abrasive slurries. Multimedia three-dimensional printing is also known, so that in some embodiments, mixed metallic-plastic items may be fabricated. In the ideal embodiment, the tools discussed herein are produced using bioresorbable, sterilizable material so that any dust or other stray material left within the patient during the procedure may be absorbed by the body. This method of manufacture results in low-cost instrumentation that is compatible with single-use application.

As used in this patent application, the terminology "for example," "for instance," "like," "such as," "comprising," "having," "including," and the like, when used with a listing of one or more elements, is open-ended, meaning that the listing does not exclude additional elements. Likewise, when preceding an element, the articles "a," "an," "the," and "said" mean that there are one or more of the elements. Moreover, directional words such as front, rear, top, bottom, upper, lower, radial, circumferential, axial, lateral, longitudinal, vertical, horizontal, transverse, and/or the like are employed by way of example and not limitation. As used herein, the term "may" is an expedient merely to indicate optionality, for instance, of an element, feature, or other thing, and cannot be reasonably construed as rendering indefinite any disclosure herein. Other terms are to be interpreted and construed in the broadest reasonable manner in accordance with their ordinary and customary meaning in the art, unless the terms are used in a context that requires a different interpretation.

Finally, the present disclosure is not a definitive presentation of an invention claimed in this patent application but is merely a presentation of examples of illustrative embodiments of the claimed invention. More specifically, the present disclosure sets forth one or more examples that are not limitations on the scope of the claimed invention or on terminology used in the accompanying claims, except where terminology is expressly defined herein. And although the present disclosure sets forth a limited number of examples, many other examples may exist now or are yet to be discovered and, thus, it is neither intended nor possible to disclose all possible manifestations of the claimed invention. In fact, various equivalents will become apparent to artisans of ordinary skill in view of the present disclosure and will fall within the spirit and broad scope of the accompanying claims. Features of various implementing embodiments may be combined to form further embodiments of the invention. Therefore, the claimed invention is not limited to the particular examples of illustrative embodiments disclosed herein but, instead, is defined by the accompanying claims.

What is claimed is:

1. A device for performing a plurality of remote operations, the device comprising:
   a handle;
   a loading tool extending from the handle;
   a spine coupled to the loading tool, the spine comprised of a plurality of chain segments, wherein each chain segment is removably coupled to an adjacent chain segment, the chain segments collectively defining a series of operational openings;

a flexible shaft disposed through the operational openings of the chain segments, the flexible shaft configured to be removed from the spine without movement of the spine;

a drill disposed on a distal end of the flexible shaft, the drill configured to couple to a plurality of tools; and a flexible outer sheath positioned around the spine.

2. The device of claim 1, wherein the outer sheath includes a plurality of grooves.

3. The device of claim 2, wherein the plurality of grooves contain a therapeutic agent.

4. The device of claim 1, wherein the drill is configured to couple to a plurality of tools at one time.

5. The device of claim 1, wherein the plurality of tools includes at least one of a tweezer tool, a scissor tool, and screw drill assembly.

6. The device of claim 1, wherein the flexible shaft is configured to rotate within the spine without corresponding movement of the spine.

7. The device of claim 1, wherein the spine is configured to bend at an angle up to 180° relative to a tip of the loading tool.

8. The device of claim 1, further comprising a strain sensor coupled to the outer sheath, the strain sensor configured to indicate a bending angle of the outer sheath.

9. A device for performing a plurality of remote operations, the device comprising:

a handle;

a loading tool extending from the handle;

a spine coupled to the loading tool, the spine comprised of a plurality of chain segments, wherein each chain segment is removably coupled to an adjacent chain segment, the chain segments collectively defining a series of operational openings;

a flexible shaft disposed through the operational openings of the chain segments, the flexible shaft configured to be removed from the spine without movement of the spine;

a drill disposed on a distal end of the flexible shaft, the drill configured to couple to a plurality of tools; and an outer sheath having a plurality of grooves containing a therapeutic agent, the outer sheath positioned around the spine.

10. The device of claim 9, wherein the outer sheath is flexible.

11. The device of claim 9, wherein the drill is configured to couple to a plurality of tools at one time.

12. The device of claim 9, wherein the flexible shaft is configured to rotate within the spine without corresponding movement of the spine.

13. The device of claim 9, wherein the spine is configured to bend at an angle up to 180° relative to a tip of the loading tool.

14. The device of claim 9, further comprising a strain sensor coupled to the outer sheath, the strain sensor configured to indicate a bending angle of the outer sheath.

15. A device for performing a plurality of remote operations, the device comprising:

a handle;

a loading tool extending from the handle;

a spine coupled to the loading tool, the spine comprised of a plurality of chain segments, wherein each chain segment is removably coupled to an adjacent chain segment, the chain segments collectively defining a series of operational openings;

a flexible shaft disposed through the operational openings of the chain segments, the flexible shaft configured to be removed from the spine without movement of the spine;

a drill disposed on a distal end of the flexible shaft, the drill configured to couple to a plurality of tools, including at least one of a tweezer tool, a scissor tool, and screw drill assembly; and an outer sheath positioned around the spine.

16. The device of claim 15, wherein the drill is configured to couple to a plurality of tools at one time.

17. The device of claim 15, wherein the flexible shaft is configured to rotate within the spine without corresponding movement of the spine.

18. The device of claim 15, wherein the spine is configured to bend at an angle up to 180° relative to a tip of the loading tool.

19. The device of claim 15, further comprising a strain sensor coupled to the outer sheath, the strain sensor configured to indicate a bending angle of the outer sheath.

20. The device of claim 15, wherein the outer sheath is flexible.

\* \* \* \* \*